United States Patent
Brophy et al.

[11] Patent Number: 6,103,198
[45] Date of Patent: Aug. 15, 2000

[54] MICROPIPETTE TIP STRIP AND METHOD

[75] Inventors: John M. Brophy, Taylorsville; West L. Price, Draper; Joseph Jeffs, Sandy, all of Utah

[73] Assignee: Sorenson Bioscience, Inc., Salt Lake City, Utah

[21] Appl. No.: 08/935,469

[22] Filed: Sep. 24, 1997

[51] Int. Cl.⁷ .................................................. B01L 3/02
[52] U.S. Cl. .................. 422/100; 73/863.32; 73/864.01; 73/864.17; 422/101; 422/102
[58] Field of Search .................. 422/100, 101, 422/102, 104; 73/863.32, 864.01, 864.14, 864.17

[56] References Cited

U.S. PATENT DOCUMENTS

| | | | |
|---|---|---|---|
| 4,215,092 | 7/1980 | Suovaniemi et al. | 422/100 |
| 4,335,621 | 6/1982 | Tervamaki et al. | 73/863.32 |
| 4,565,100 | 1/1986 | Malinoff | 422/100 |
| 4,659,677 | 4/1987 | Golover et al. | 73/863.32 |
| 4,707,337 | 11/1987 | Jeffs et al. | 422/100 |
| 4,721,680 | 1/1988 | Jeffs et al. | 436/180 |
| 4,801,434 | 1/1989 | Kido et al. | 422/100 |
| 4,824,642 | 4/1989 | Lynman et al. | 73/863.32 |
| 4,925,629 | 5/1990 | Schramm | 422/100 |
| 4,948,564 | 8/1990 | Root et al. | 422/104 |
| 5,021,217 | 6/1991 | Oshikubo | 422/100 |
| 5,032,343 | 7/1991 | Jeffs et al. | 264/320 |
| 5,110,555 | 5/1992 | Moore et al. | |
| 5,110,556 | 5/1992 | Lyman et al. | 422/102 |
| 5,343,909 | 9/1994 | Goodman | 73/863.32 |
| 5,496,523 | 3/1996 | Gazit et al. | 422/100 |

FOREIGN PATENT DOCUMENTS

| | | |
|---|---|---|
| 0 034 438 | 8/1981 | European Pat. Off. . |
| 0 093 355 | 11/1983 | European Pat. Off. . |
| 0 127 267 | 12/1984 | European Pat. Off. . |
| 0 266 155 | 5/1988 | European Pat. Off. . |
| 2115719 | 9/1983 | United Kingdom . |

*Primary Examiner*—Jan Ludlow
*Attorney, Agent, or Firm*—Trask Britt

[57] ABSTRACT

A pipette tip device. The device includes a plurality of interconnected pipette tips disposed in substantially parallel orientation and in side-by-side alignment. The tips are hollow and each tip includes a tip body and a flattened distal extremity. The flattened distal extremities are all disposed in substantial co-planar alignment common to a single plane to thereby enable simultaneous insertion of the flattened distal extremities between closely spaced-apart plate surfaces.

29 Claims, 1 Drawing Sheet

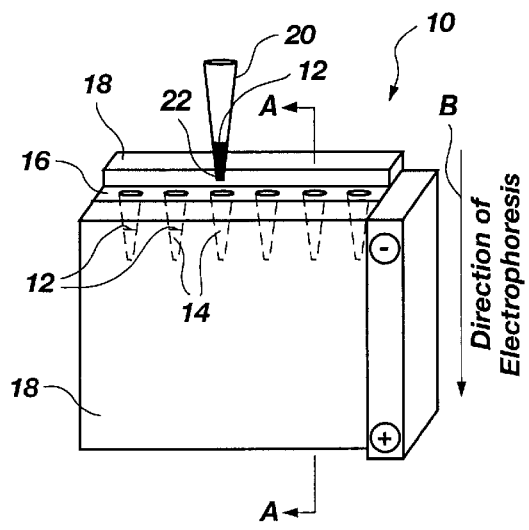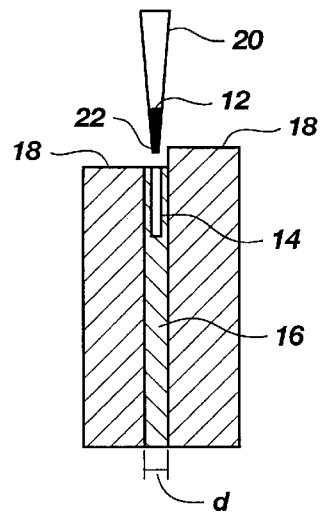
Fig. 1
*(PRIOR ART)*
Fig. 2
*(PRIOR ART)*
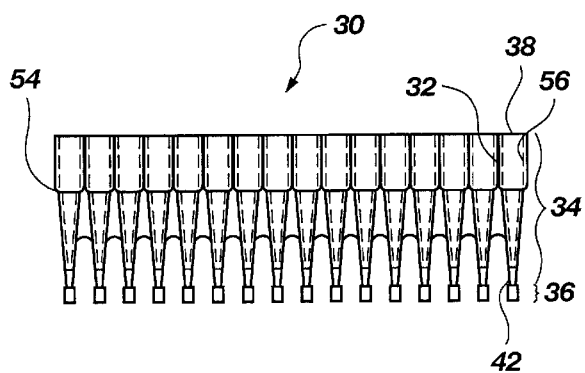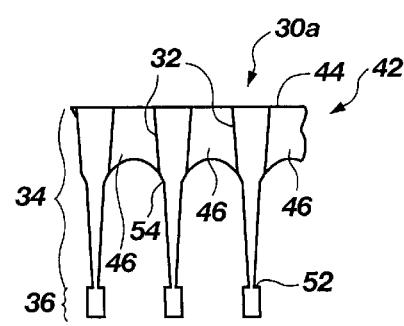
Fig. 3
Fig. 4
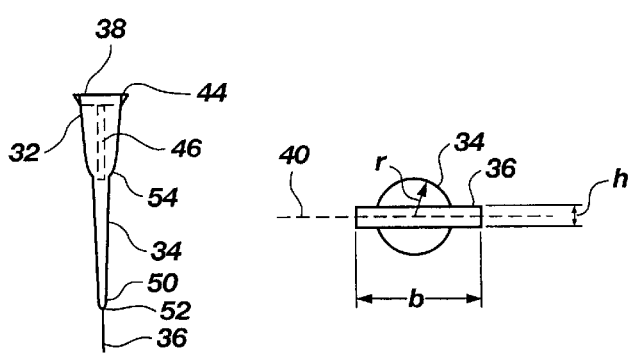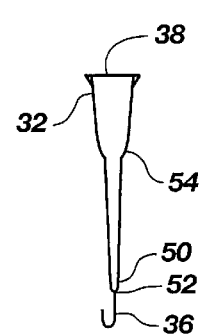
Fig. 5
Fig. 6
Fig. 7

MICROPIPETTE TIP STRIP AND METHOD

BACKGROUND OF THE INVENTION

1. The Field of the Invention

The present invention relates generally to micropipette tips used in electrophoresis processes such as DNA sequencing. More particularly, it concerns a plurality of interconnected tips each having thin flattened extremities for simultaneously dispensing a plurality of biological samples between electrophoresis plates.

2. The Background Art

Proteins play a crucial role in nearly all biological processes, including catalysis, transport, coordinated motion, excitability, and the control of growth and differentiation. By studying and analyzing proteins, scientists have been able to provide important practical knowledge useable in a vast array of applications, from biomedical techniques to criminology, and many others.

The prior art methods and apparatus for studying proteins fall generally under three categories of approach, namely, electrophoresis, ultracentrifugation, and chromatography. One of the major goals in protein study is to determine how amino acid sequences specify the conformations of proteins. In electrophoresis, this is accomplished by separating and displaying the molecules of proteins and other macromolecules, such as DNA and RNA, by their molecular weight. A molecule having a net charge will move in an electric field, hence the term electrophoresis. Protein samples are dispensed in a holding matrix, an electric field is applied, and the charge-carrying molecules separate according to their weight. Once the molecules of a protein are separated and displayed in accordance with their molecular weight, the display can be studied to determine the protein's amino acid sequence.

The structural means for accomplishing "vertical electrophoresis" typically includes two opposing, vertically-disposed transparent plates disposed in a parallel, closely spaced-apart orientation for holding porous sequencing gel therebetween, such as polyacrylamide gel. Protein samples are dispensed into the gel, which is capable of suppressing convective currents produced by small temperature gradients (a requirement for effective separation), and the gel also operates as a "molecular sieve" that enhances the separation of molecules by their molecular weight. Molecules that are small compared with the pores in the gel readily move through the gel, while molecules larger than the gel pores are rendered essentially immobile. Intermediate-size molecules move through the gel with various degrees of facility. However, the molecular weights of the molecules is the principle factor that determines the separation among charge-carrying molecules, under the force of the electric field.

One of the challenges in properly conducting electrophoretic analysis is the difficulty of dispensing the protein samples into the gel with reproducible quantitative accuracy. The sample plates are spaced extremely closely together, for example by 0.20 millimeters. A lab technician must extract samples of the protein with a single channel pipettor or syringe and dispense them into individual wells formed in the sequencing gel, repeatably aspirating and dispensing each sample one at a time in the same micro-volume quantity. This requires a highly skilled technician and a large amount of time with little room for error, especially when the study involves a valuable biological sample in short supply. Accordingly, there is a need for a method and device capable of placing multiple biological samples between the electrophoresis plates more quickly and more accurately.

OBJECTS AND SUMMARY OF THE INVENTION

It is therefore an object of the present invention to provide a pipette tip device capable of placing biological samples more quickly and accurately.

It is another object of the present invention to provide such a pipette tip device capable of placing a plurality of biological samples simultaneously between closely spaced electrophoretic plates.

The above objects and others not specifically recited are realized in a specific illustrative embodiment of a pipette tip device. The device includes a plurality of interconnected pipette tips disposed in substantially parallel orientation and in side-by-side alignment. The tips are hollow and each tip includes a tip body and a flattened distal extremity. The flattened distal extremities are all disposed in substantial co-planar alignment common to a single plane to thereby enable simultaneous insertion of the flattened distal extremities between closely spaced-apart plate surfaces.

Additional objects and advantages of the invention will be set forth in the description which follows, and in part will be apparent from the description, or may be learned by the practice of the invention. The objects and advantages of the invention may be realized and obtained by means of the instruments and combinations particularly pointed out in the appended claims.

BRIEF DESCRIPTION OF THE DRAWINGS

The above and other objects, features and advantages of the invention will become apparent from a consideration of the subsequent detailed description presented in connection with the accompanying drawings in which:

FIG. 1 is a perspective, schematic view of a prior art apparatus for conducting electrophoresis;

FIG. 2 is a side, cross-sectional view of the prior art apparatus of FIG. 1, taken along section A—A;

FIG. 3 is a front view of a pipette tip strip, made in accordance with the principles of the present invention;

FIG. 4 is side, break-away view of an alternative embodiment of the pipette tip strip of FIG. 3;

FIG. 5 is a side view of the pipette tip strip of FIG. 4;

FIG. 6 is a bottom view of one channel of the pipette tip strip of FIG. 4; and

FIG. 7 is a side view of the pipette tip strip of FIGS. 4–5, showing a flexible distal extremity of an end tip bent upwardly into a U-shaped conformation.

DETAILED DESCRIPTION

For the purposes of promoting an understanding of the principles in accordance with the invention, reference will now be made to the embodiments illustrated in the drawings and specific language will be used to describe the same. It will nevertheless be understood that no limitation of the scope of the invention is thereby intended. Any alterations and further modifications of the illustrated device, and any additional applications of the principles of the invention as illustrated herein, which would normally occur to one skilled in the relevant art and in possession of this disclosure, are to be considered within the scope of the invention claimed.

Applicants have discovered that electrophoresis procedures are greatly enhanced by withdrawing a plurality of biological samples and inserting them simultaneously in the sequencing gel contained between electrophoretic plates.

When conducting electrophoresis, technicians have had to use single-channel pipettors or syringes to place multiple samples, one-by-one, within the sequencing gel contained between the plates, as shown in FIG. 1. By interconnecting a plurality of tips together and flattening the ends of the tips in co-planar alignment as shown in FIG. 3, applicants have provided a device which greatly enhances the speed and accuracy by which the technician may accomplish electrophoresis.

In FIGS. 1–2 is shown an electrophoresis device, designated generally at 10. Typically, biological samples 12 (such as DNA or other proteins) are dispensed one at a time in wells 14 formed within a thin film of sequencing gel 16 held sandwiched between opposing plates 18. A cover (not shown) may be placed over the gel chamber, and a voltage is applied to the gel 16. Charge-carrying molecules forming the samples 12 migrate downwardly, as indicated by arrow B, and are separated by the applied voltage in accordance with their molecular weight.

The samples 12 are dispensed into the gel 16 by a micropipette tip 20, which is carried upon a pipettor (not shown). The plates 18 are spaced apart by a distance d as shown in FIG. 1, which might illustratively comprise 0.20 millimeters. Because of the difficulty in directing the tip 20 into such a narrow space, one of the plates 18 is higher than the other to facilitate easier channeling of the tip 20 into the space d between the plates 18. The main body of tip 20 is generally several times wider than the space d defined between the two plates 18, requiring the distal end 22 of the tip 20 to be adequately narrow to fit between the plates 18.

In FIG. 3 is shown one embodiment of the invention, in the form of a pipette tip device designated generally at 30. The device 30 includes a plurality of interconnected pipette tips 32 disposed in substantially parallel orientation and in side-by-side alignment, such that said tips 32 form a substantially straight path. The tips 32 are hollow and each comprises a tip body 34 and a flattened distal extremity 36. It is understood that the device 30 may include any number of interconnected tips 32. It is to be understood that the phrase "pipette tip," as used herein, shall be construed broadly to cover any kind of hollow dispensing tip regardless of whether the tip is actually used on a pipettor instrument, syringe or other dispensing device.

The flattened distal extremities 36 are all disposed in substantial co-planar alignment common to a single plane to thereby enable simultaneous insertion of said flattened distal extremities between the closely spaced-apart plate surfaces 18 of FIGS. 1–2. An interior bore of the tips 32 extends from an open upper end 38 of each tip 32 through the flattened distal extremity 36. A technician may simply place samples into each tip 32, then place the distal extremities 36 simultaneously into the pre-formed wells 14 (FIGS. 1–2) formed in the sequencing gel and dispense the samples simultaneously.

As shown in FIGS. 3–6, the distal extremities 36 each have a cross-sectional shape that is wider in a first dimension and narrower in a second dimension orthogonal to said first dimension. More specifically, each distal extremity 36 is wider in dimension b than in dimension h, as shown most clearly in FIG. 6.

Preferably, the distal extremities 36 of the tips 32 are disposed in alignment such that the wider, first dimensions of the cross sections of said distal extremities 36 extend discontinuously in a common direction along a single straight path. This is another way of saying the distal extremities 36 are disposed in a substantial co-planar alignment. The distal extremities 36 are so thin, preferably less than 0.20 millimeters, that the tip body 34 of each tip 32 is wider in all dimensions than the second, narrower dimension (h in FIG. 6) of the distal extremity 36 of said tip 32.

Preferably, the tips 32 are made of a suitable resilient plastic, as known in the art of micropipette tips, and the flattened distal extremities 36 are flexible and have elastic memory. Most preferably, each flattened distal extremity 36 possesses a sufficient amount of flexibility to enable bending of said distal extremity 36 into a U-shaped conformation without causing failure of the plastic material forming said distal extremity 36, as shown most clearly in FIG. 7.

Referring now more particularly to FIG. 6, it is illustrated generally that the tip body 34 has a cross-sectional shape having a first area of inertia about a center line 40 bisecting said cross-sectional shape that is more than ten times greater than a second area of inertia of a cross-sectional shape of the distal extremity 36 about said same center line 40. This is determined by the mathematical equations for computing areas of inertia as known in the relevant field of engineering, including the following equations:

$$I_x(\text{rectangle}) = \tfrac{1}{12} bh^3; \text{ and}$$

$$I_x(\text{circle}) = \tfrac{1}{4} \pi r^4;$$

where $I_x$ = area of inertia about an x axis (depicted as centerline 40 in FIG. 6)

b = "base" dimension b shown in FIG. 6, and h = "height" dimension h shown in FIG. 6 r = "radius" dimension r shown in FIG. 6.

It is to be understood that the phrase "area of inertia" as used herein shall refer to an inertia of area defined by the outer perimeter of a body, regardless of whether that body is hollow or solid. Applicants realize that the similar phrase "moment of inertia" for a hollow body such as the tip body 34 and distal extremity 36 contemplates an inertia produced by a wall thickness of the body, and the phrase "area of inertia" is therefore defined herein to be distinct from a "moment of inertia" in that an "area of inertia" remains the same regardless of whether the subject body is hollow or solid while the "moment of inertia" differs when the subject body is hollow or solid. Further, the "area of inertia" will be equivalent to the "moment of inertia" for a subject body that is solid.

Most preferably, the tip body 34 has a cross-sectional shape varying in size along a length of said tip body 34 because of a radial inward taper effect in the tip 32, such that a smallest cross-sectional shape of said tip body 34 (corresponding to a narrowest portion 42 shown in FIG. 3) has a first area of inertia about the center line 40 (FIG. 6) that is more than ten times greater than a second area of inertia of a cross-sectional shape of the distal extremity 36 about said same center line 40. The first area of inertia is preferably more than 100 times greater than the second area of inertia, and preferably more than 200 times greater than the second area of inertia, and preferably more than 400 times greater than the second area of inertia, and preferably more than 600 times greater than the second area of inertia, and preferably more than 800 times greater than the second area of inertia. Because of the aforementioned taper, the tip body 34 has an exterior surface that constitutes a frustoconical shape. It will be appreciated that these preferred differences in areas of inertia may be presented regardless of the cross-sectional shapes of the tip body 34 and distal extremity 36.

Referring to FIGS. 3–4, it is shown that the flattened distal extremity 36 comprises less than 40% of a total length of the tip 32. More preferably, the flattened distal extremity 36 comprises less than 30% of a total length of the tip 32. Most preferably, the flattened distal extremity 36 comprises less than 20% of a total length of the tip 32.

Referring to FIGS. 4–5, the pipette tip device 30a further comprises a support frame 42 interconnecting the plurality of tips 32, said frame 42 having a T-shaped cross section formed by an upper surface 44 and a plurality of discontinuous brace members 46 extending downwardly from said upper surface and between the pipette tips 32. Each brace member 46 that extends between adjacent pipette tips 32 is fixedly attached to said adjacent tips 32, and each tip 32 has an open upper end 38 fixedly attached to the upper surface 44 of the support frame 42 such that said tips 32 and said support frame 42 cooperatively form a one-piece, unitary member.

The phrase "fixedly attached" or "fixedly secured" as used herein shall refer broadly to the condition of one item being attached to another such that their separation would require breaking, melting or other failure of the material.

Each tip 32 preferably includes an exterior, abrupt transition section 50 (shown most clearly in FIGS. 5 and 7) between the tip body 34 and the flattened distal extremity 36 that forms an enlargement in comparison to said distal extremity 36. The enlargement extends outwardly from opposing sides of an interior end 52 of the distal extremity 36 and operates to limit an insertion depth of the tip 32 when said distal extremity 36 is inserted into a space that is narrower than said enlargement. Most preferably, each tip 32 also includes an open upper end 38 and a second exterior abrupt transition section 54 located between the enlargement and said open upper end.

It is to be understood that the pipette tip devices 30 and 30a of FIGS. 3–4 may be fabricated using any suitable method. For example, the device 30a may be first injection molded such that each tip 32 is formed in the manner of a standard micropipette tip (except that multiple tips are interconnected by support frame 42) without any flattening at the distal end, after which the tips 32 may be placed upon tiny mandrels (not shown) and heat pressed at the tips to form the flattened distal extremities 36. Alternatively, the devices 30 and 30a may be formed by extrusion, or by any suitable process. Any process of injection molding, extrusion, heat pressing, or any other method now known or later discovered, that is used to form the devices 30 and/or 30a are within the scope of the present invention.

In a generic sense, the plurality of interconnected tips 32 are initially molded from uncured plastic material, and the flattened tips 36 are formed after said uncured plastic material has cured, by heating and pressing the distal ends 36 of the tips 32. But the plurality of interconnected tips 32 could also be formed by a molding process of uncured plastic material, including formation of the distal extremities 36 by molding.

It will be appreciated that the devices 30 and 30a may be defined in several different ways, all of which are within the scope of the present invention. For example, the distal extremities 36 need not be flattened, as long as they differ in cross-sectional area from the tip body 34. With this in mind, the invention may be described in terms of the tips 32 being hollow and each tip comprising a tip body 34 and a distal end portion 36, said tip body 34 and distal end portion 36 having substantially different cross-sectional shapes. Or still further, the tip bodies 34 may be described as having a circular cross section, with the distal end portion 36 having a non-circular cross section. It is to be understood that the distal ends 36 may be described as being aligned in a common direction along a single path, regardless of their cross-sectional shape and regardless of whether the single path is straight or non-straight.

The tips 32 may further be described as having a main body 34 tapering radially inwardly in an upper-to-lower direction, each tip 32 terminating in a distal extremity 36 having a cross-sectional shape that is wider in a first dimension (dimension b in FIG. 6) and narrower in a second dimension (dimension h in FIG. 6) orthogonal to said first dimension, there being an abrupt transition section 50 intercoupling and disposed between the main body 34 and the distal extremity 36.

The tips are hollow and define a throughpassage 56 therein. The throughpassage 56 extends through the tip body 34 and distal end portion 36. The portion of the throughpassage 56 which resides at the narrowest portion 42 of the tip body 34 has a cross-sectional area that is preferably about ten times the cross-sectional area of the throughpassage residing in the distal extremity portion 36. In applicants' present embodiment, the cross-sectional area of the throughpassage 56 residing in the narrowest portion 42 of the tip body 34 is about 0.00045 square inches, while the cross-sectional area of the throughpassage in the distal extremity 36 is about 0.000045 square inches. It is preferred that the cross-sectional area of the throughpassage 56 in the narrowest portion 42 be at least three times, and more preferably at least eight times, and most preferably ten times, the cross-sectional area of the portion of the throughpassage 56 residing in the distal extremity 36. It may also be any multiplicity of times, such as twenty, fifty, one hundred or more, if desired.

It will be appreciated that although multi-channel pipettors could be used to carry individual pipette tips formed to have flattened distal extremities (in contrast with interconnected tips 32 of the present invention), this has disadvantages that are solved by the present invention. It is critical that the flattened distal extremities be disposed in co-planar alignment for proper dispensing of the biological samples in an efficient manner (or in some suitable alignment in a common direction if the distal ends 36 are narrow but not flattened, a condition in which the term "co-planar" may not apply). Since individual pipette tips are simply stacked in racks in random orientation, their flattened distal extremities would not be properly disposed in co-planar alignment when dispensed in the multi-channel pipettor. This would require the technician to engage in a laborious and time-consuming process to align the distal extremities by hand while the tips are held in the multi-channel pipettor, and any advantage of accuracy and efficiency beyond a single-tip, one-by-one dispensing approach would be nominal.

In accordance with the features and combinations described above, a preferred method of inserting a plurality of biological samples between closely-spaced surfaces includes the steps of:

(a) selecting a plurality of fixedly interconnected pipette tips terminating in distal ends, said distal ends having non-circular cross sections and being thereby wider in a first dimension and narrower in a second dimension orthogonal to said first dimension;

(b) dispensing biological samples in the pipette tips;

(c) inserting the distal ends of the plurality of interconnected tips substantially simultaneously between two closely spaced surfaces and permitting the biological samples to transfer from the fixedly interconnected tips; and (d) removing the distal ends of the interconnected tips from between the closely spaced surfaces.

It is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements.

What is claimed is:

1. A pipette tip device comprising:
   a plurality of interconnected pipette tips disposed in substantially parallel orientation and in side-by-side alignment;
   wherein the tips are hollow and each tip comprises a tip body and a flattened distal extremity, said flattened distal extremities all being discontinuous and disposed in substantial co-planar alignment common to a single plane to thereby enable simultaneous insertion of said flattened distal extremities between closely spaced-apart plate surfaces.

2. The pipette tip device of claim 1, wherein the distal extremities each have a cross-sectional shape that is wider in a first direction than in a second direction orthogonal to said first direction.

3. The pipette tip device of claim 2, wherein the distal extremities of the tips are disposed in alignment such that the wider, first dimensions of the cross sections of said distal extremities extend discontinuously in a common direction along a single path.

4. The pipette tip device of claim 2, wherein the tip body of each tip is wider in all dimensions than the second dimension of the distal extremity of said tip.

5. The pipette tip device of claim 1, wherein the flattened distal extremities are flexible.

6. The pipette tip device of claim 5, wherein each flattened distal extremity possesses a sufficient amount of flexibility to enable bending of said distal extremity into a U-shaped conformation without causing failure of material forming said distal extremity.

7. The pipette tip device of claim 1, wherein the tip body has a cross-sectional shape having a first area of inertia about a center line bisecting said cross-sectional shape that is more than ten times greater than a second area of inertia of a cross-sectional shape of the distal extremity about said same center line.

8. The pipette tip device of claim 1, wherein the tip body has a cross-sectional shape varying in size along a length of said tip body, and wherein a smallest cross-sectional shape of said tip body has a first area of inertia about a center line bisecting said smallest cross-sectional shape that is more than ten times greater than a second area of inertia of a cross-sectional shape of the distal extremity about said same center line.

9. The pipette tip device of claim 8, wherein the first area of inertia is more than 100 times greater than the second area of inertia.

10. The pipette tip device of claim 8, wherein the first area of inertia is more than 200 times greater than the second area of inertia.

11. The pipette tip device of claim 8, wherein the first area of inertia is more than 400 times greater than the second area of inertia.

12. The pipette tip device of claim 8, wherein the first area of inertia is more than 600 times greater than the second area of inertia.

13. The pipette tip device of claim 8, wherein the first area of inertia is more than 800 times greater than the second area of inertia.

14. The pipette tip device of claim 1, wherein the flattened distal extremity comprises less than 40% of a total length of the tip.

15. The pipette tip device of claim 1, wherein the flattened distal extremity comprises less than 30% of a total length of the tip.

16. The pipette tip device of claim 1, wherein the flattened distal extremity comprises less than 20% of a total length of the tip.

17. The pipette tip device of claim 1, further comprising:
    a plurality of discontinuous brace members disposed between the pipette tips.

18. The pipette tip device of claim 1, further comprising:
    an upper surface, wherein each tip has an open upper end fixedly attached to the upper surface.

19. The pipette tip device of claim 1, further comprising:
    a support frame interconnecting the plurality of tips, said support frame having a T-shaped cross section formed by an upper surface and a plurality of discontinuous brace members extending downwardly from said upper surface and between the pipette tips;
    wherein each brace member that extends between adjacent pipette tips is fixedly attached to said adjacent tips, and wherein each tip has an open upper end fixedly attached to the upper surface of the support frame such that said tips and said support frame cooperatively form a one-piece, unitary member.

20. The pipette tip device of claim 1, wherein each tip includes an exterior, abrupt transition section between the tip body and the flattened distal extremity that forms an enlargement in comparison to said distal extremity, said enlargement extending outwardly from opposing sides of an interior end of said distal extremity and operating to limit an insertion depth of the tip when said distal extremity is inserted into a space that is narrower than said enlargement.

21. The pipette tip device of claim 20, wherein each tip includes an open upper end and a second exterior abrupt transition section located between the enlargement and said open upper end.

22. The pipette tip device of claim 1, wherein the tip body includes an exterior surface having a frustoconical shape.

23. The pipette tip device of claim 1, wherein the plurality of interconnected pipette tips forms a one-piece unitary member.

24. The pipette tip device of claim 1, wherein the plurality of interconnected pipette tips is made from a resilient plastic material.

25. The pipette tip device of claim 1, wherein the plurality of interconnected tips is initially molded from uncured plastic material, and wherein the flattened tips are formed after said uncured plastic material has cured, by heating and pressing distal ends of the tips.

26. The pipette tip device of claim 1, wherein the plurality of interconnected tips is formed by a molding process of uncured plastic material, including formation of the distal extremities.

27. The pipette tip device of claim 1, wherein the side-by-side alignment of the pipette tips forms a substantially straight path.

28. A pipette tip device comprising:
    a plurality of interconnected pipette tips disposed in substantially parallel orientation and in side-by-side alignment;
    a plurality of discontinuous brace members extending between the pipette tips;
    wherein the tips are hollow and each tip comprises a tip body and a flattened distal extremity, said flattened distal extremities all being disposed in substantial co-planar alignment common to a single plane to thereby enable simultaneous insertion of said flattened distal extremities between closely spaced-apart plate surfaces;

wherein the distal extremities each have a cross-sectional shape that is wider in a first direction than in a second direction orthogonal to said first direction;

wherein the distal extremities of the tips are disposed in alignment such that the wider, first dimensions of the cross-sections of said distal extremities extend discontinuously in a common direction along a single path;

wherein the tip body of each tip is wider in all dimensions than the second dimension of the distal extremity of said tip;

wherein the flattened distal extremities are flexible;

wherein each flattened distal extremity possesses a sufficient amount of flexibility to enable bending of said distal extremity into a U-shaped conformation without causing failure of material forming said distal extremity;

wherein the tip body has a cross-sectional shape varying in size along a length of said tip body, and wherein a smallest cross-sectional shape of said tip body has a first area of inertia about a center line bisecting said smallest cross-sectional shape that is more than 100 times greater than a second area of inertia of a cross-sectional shape of the distal extremity about said same center line;

wherein the flattened distal extremity comprises less than 40% of a total length of the tip;

wherein each brace member that extends between adjacent pipette tips is fixedly attached to said adjacent tips;

wherein each tip includes an exterior, abrupt transition section between the tip body and the flattened distal extremity that forms an enlargement in comparison to said distal extremity, said enlargement extending outwardly from opposing sides of an interior end of said distal extremity and operating to limit an insertion depth of the tip when said distal extremity is inserted into a space that is narrower than said enlargement;

wherein the tip body includes an exterior surface having a frustoconical shape;

wherein the plurality of interconnected pipette tips and the support frame are made from a resilient plastic material;

wherein the side-by-side alignment of the pipette tips forms a substantially straight path.

29. The pipette tip device of claim 28, further comprising:

a support frame interconnecting the plurality of tips, said support frame having a T-shaped cross section formed by an upper surface and the plurality of discontinuous brace members, said brace members extending downwardly from said upper surface and between the pipette tips;

wherein each tip has an open upper end fixedly attached to the upper surface of the support frame such that said tips and said support frame cooperatively form a one-piece, unitary member.

* * * * *